United States Patent [19]

Moran

[11] 4,039,288
[45] Aug. 2, 1977

[54] AUTOMATIC CHEMICAL TESTING APPARATUS INCORPORATING IMPROVED CONVEYOR SYSTEM

[75] Inventor: John J. Moran, Houston, Tex.

[73] Assignee: Hycel, Inc., Houston, Tex.

[21] Appl. No.: 725,269

[22] Filed: Sept. 21, 1976

[30] Foreign Application Priority Data

Mar. 17, 1976 United Kingdom ............... 10685/76

[51] Int. Cl.² ........................ G01N 1/10; G01N 33/16
[52] U.S. Cl. ................................... 23/253 R; 141/130
[58] Field of Search ................. 23/230 R, 253 R, 259; 141/130

[56] References Cited

U.S. PATENT DOCUMENTS

| | | | |
|---|---|---|---|
| 3,644,095 | 2/1972 | Netheler et al. ........................ | 23/259 |
| 3,728,079 | 4/1973 | Moran ................................. | 23/259 X |
| 3,854,879 | 12/1974 | Figueroa ............................ | 23/230 R |
| 3,985,508 | 10/1976 | Williams ............................ | 23/253 R |

*Primary Examiner*—R.E. Serwin
*Attorney, Agent, or Firm*—Timothy L. Burgess; Robert P. Cogan

[57] ABSTRACT

In an automatic chemical testing apparatus, a reaction loop conveyor carries rows of reaction containers in a path including an upper, forward path in a direction normal to the rows. Samples for analysis are provided to the reaction conveyor from a sample source. An improved system is provided in which sample source means synchronized with the reaction conveyor index successive sample containers to an aspiration station adjacent to one row in the forward path of the reaction conveyor. The sample source means may be a sample conveyor consisting of sample container holders linked together.

18 Claims, 6 Drawing Figures

AUTOMATIC CHEMICAL TESTING APPARATUS INCORPORATING IMPROVED CONVEYOR SYSTEM

BACKGROUND OF THE INVENTION

The present invention relates to automatic chemical testing apparatus and more particularly to improved means for sample handling therein.

The present invention comprehends an improvement in the type of automatic chemical testing apparatus disclosed in commonly assigned U.S. Pat. No. 3,622,279 issued Nov. 23, 1971 to John J. Moran, the disclosure of which is incorporated herein by reference. The disclosures of commonly assigned U.S. Pats. Nos. 3,672,477; 3,716,338; 3,723,066; 3,728,079; 3,728,080; and 3,762,879 all relating to the same type of apparatus are also incorporated herein by reference. In this type of apparatus, a loop reaction conveyor is provided having an upper path, which is a forward path, and a lower, return path. The conveyor is substantially horizontally disposed. The conveyor comprises conveyor slats extending transversely for motion in a longitudinal direction. Each conveyor slat supports reaction containers. In the upper path, the slats move from a sample dispensing station at which aliquots of sample, generally human serum, are dispensed into selected reaction containers in a slat, which may also be referred to as a row. Corresponding reaction containers in adjacent slats define columns, and each column defines a channel for performance of a particular clinical chemistry. As a reaction container progresses in its column, reagents are added thereto from reagent dispensing means positioned over the loop conveyor. At the end of a row reacted contents are aspirated from the reaction container and analyzed, preferably spectrophotometrically.

Serum from one sample at a time is provided to sample dispensing means. The sample dispensing means then provides aliquots to the selected sample containers. During the next cycle, aliquots of a next serum sample must be delivered by the same dispensing means to a next row of reaction containers. It is very important that there be no carry over from one sample to the next in the dispensing means. This was successfully accomplished in the apparatus of the above-cited patents to Moran by moving the dispensing means to a sample table for aspiration of a sample and then moving the dispensing means to a dispensing station for dispensing to the sample cups. The sample had to travel through a conduit of minimum length, which conduit was washed after each delivery cycle to prevent carry over. This is to be distinguished from such systems as that disclosed in U.S. Pat. No. 3,799,744 issued Mar. 26, 1974 to Jones in which diluted samples travel through elongated conduits.

It is desirable to provide a reaction conveyor and sample supply system in which samples and their containers are conveniently and efficiently handled.

SUMMARY OF THE INVENTION

It is therefore an object of the present invention to provide in an automatic chemical analyzer having a reaction loop conveyor and improved sample handling means providing for minimum travel between a sample source and means for dispensing sample aliquots to reaction containers.

It is also an object of the present invention to provide an automatic chemical testing apparatus having a reaction loop conveyor and a sample loop conveyor for supplying the sample to the reaction container.

It is a further object of the present invention to provide apparatus of the type described in which samples may be conveniently and efficiently handled.

It is yet another object of the present invention to provide apparatus of the type described in which samples are also conveniently presented for identification by sample identification means.

Briefly stated in accordance with the present invention, there is provided an automatic chemical testing apparatus comprising a first reaction loop conveyor having an upper forward path and a lower return path moving in longitudinal directions, with the conveyor consisting of slats or rows each extending in a transverse reaction and supporting reaction containers. Sample aspiration and dispensing means are mounted over one row. A sample source on the preferred form is a second, sample conveyor having drive means rotating about axes perpendicular to the axis of the first conveyor drive means. The second conveyor is indexed in synchronism with the first conveyor. The sample source delivers successive samples to an aspiration station positioned in registration with the sample aspiration and dispensing means.

BRIEF DESCRIPTION OF THE DRAWINGS

The means by which the foregoing object and features of invention are achieved are pointed out with particularity in the claims forming the concluding portion of these specifications. The invention, both as to its organization and manner of operation, may be further understood by reference to the following drawings taken in connection with the following description.

Of the drawings.

DESCRIPTION OF THE PREFERRED EMBODIMENT

Figure 1:
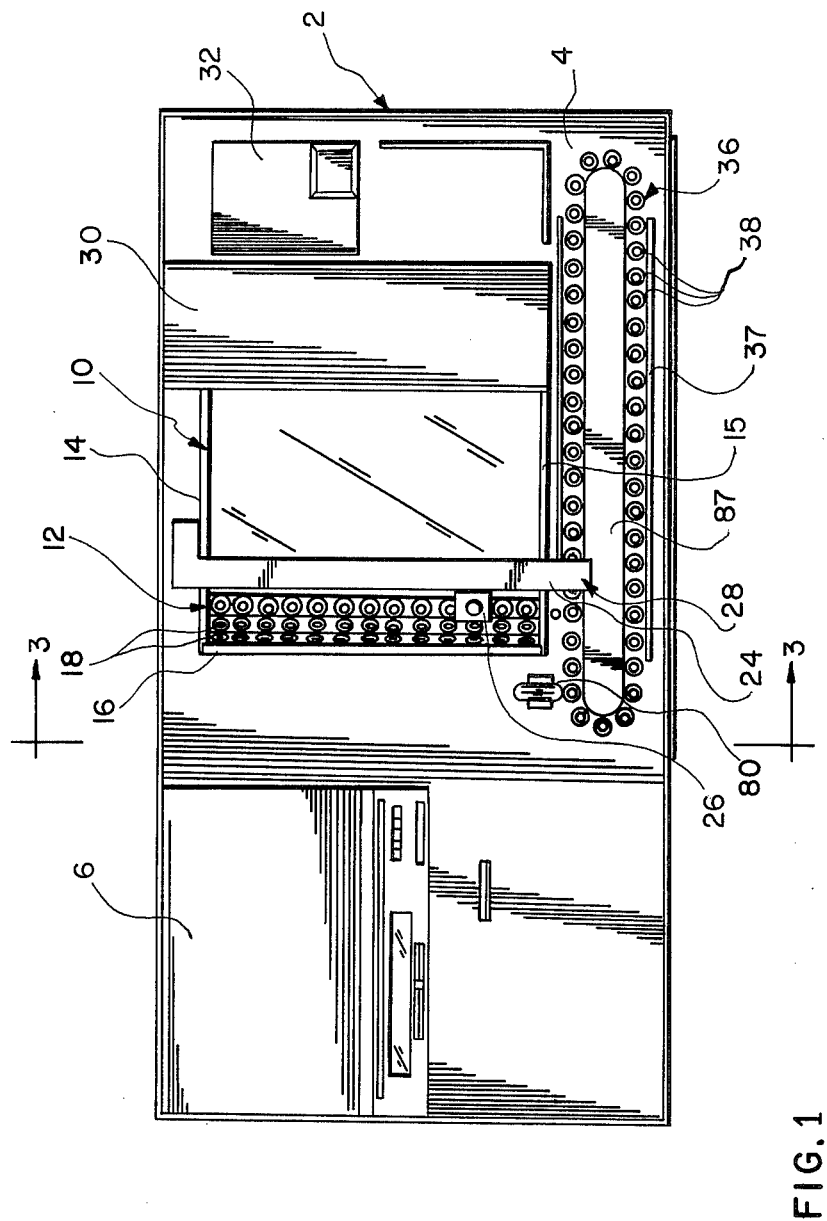
FIG. 1 is a plan view of an automatic chemical analyzer constructed in accordance with the present invention.
Figure 2:
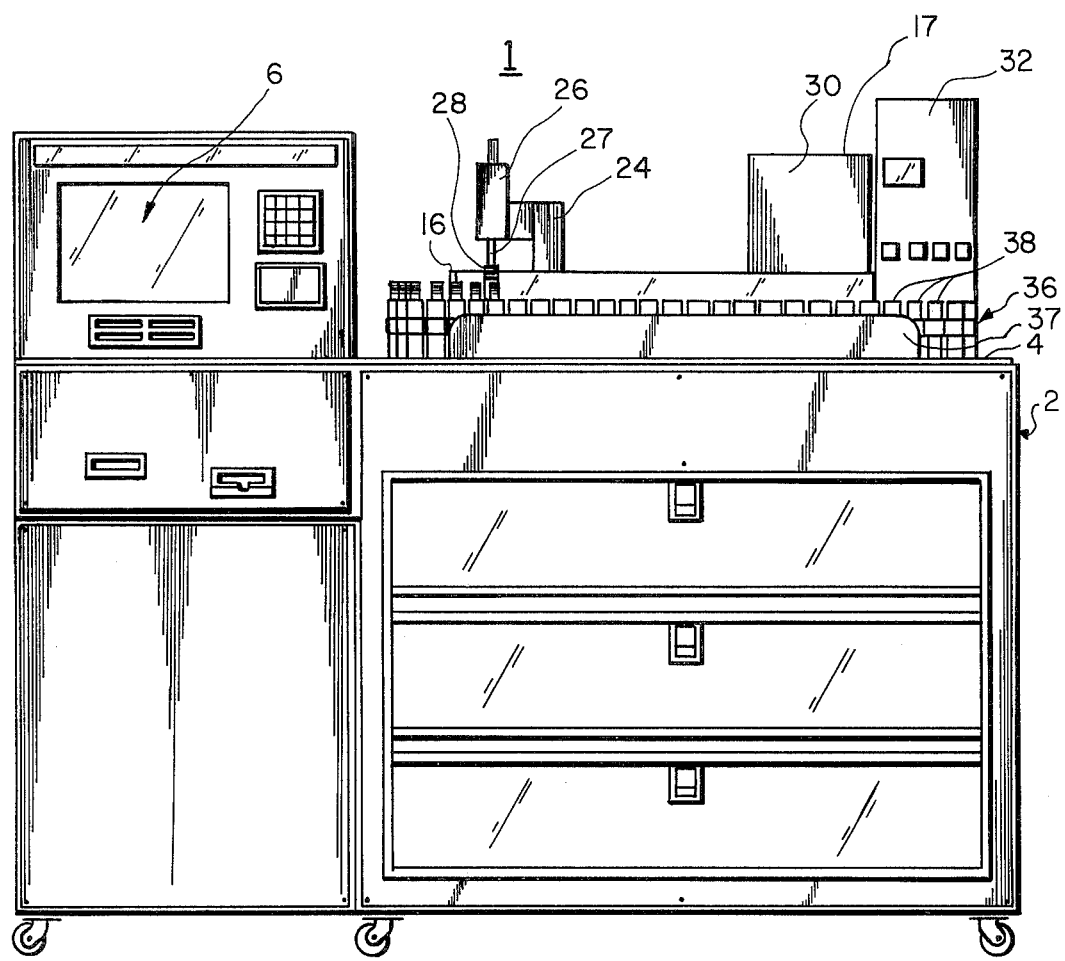
FIG. 2 is a front elevation of the apparatus of FIG. 1.

Referring to FIGS. 1 and 2 together which are respectively a plan and front elevation, automatic chemical testing apparatus constructed in accordance with the present invention is illustrated. The construction and operation of the present apparatus is briefly described here and further reference should be had to the above-cited patents to Moran whose disclosures have been incorporated herein by reference for a description of details of sample dispensing, reagent dispensing, aspiration and analysis of reacted contents and further mechanical features not detailed herein. The analyzer 1 comprises a housing 2 for housing power supplies, water purification means and reagents. The housing 2 comprises an upper surface 4, for closing the housing 2 and supporting certain components. The housing 2 may further comprise keyboard. a display and control means 6 for replacing the recorder and control means of the above-cited patents to Moran.

Figure 3:
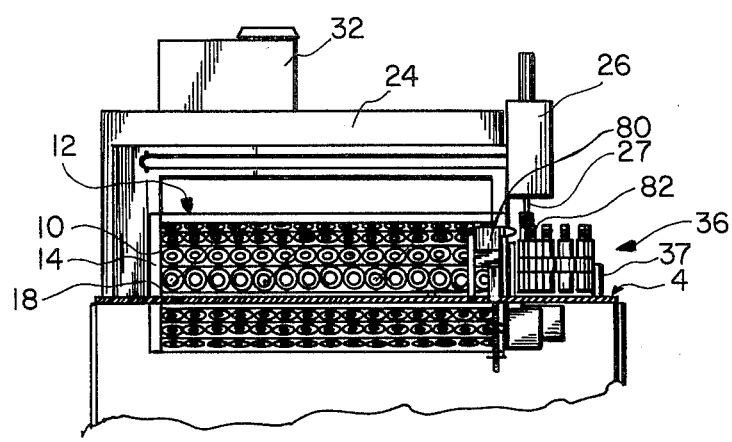
FIG. 3 is an elevation taken along section lines 3—3 of FIG. 1.

Projecting through the upper surface 4 are conveyor support means 10 spatially defining reaction means and surrounding a first, reaction conveyor 12, as seen with reference to FIGS. 1 and 3. Slide walls 14 and 15 of the support means 10 surround the conveyor 12 at transverse sides thereof, and are joined by transversely extending walls 16 and 17 at opposite longitudinal ends thereof. As further seen with respect to FIGS. 1 and 3, the conveyor 12 consists of longitudinally extending slats or sections or rows 18 mounted for movement in a longitudinal direction. The conveyor 12 has an upper, forward path and a lower return path. In the present embodiment, the forward direction in the upper path is from left to right in FIGS. 1, 2 and 5. A drive means 24 on which a movable aspiration dispensing means 26 is mounted is supported over the first conveyor 12. The aspiration and dispensing means 26 having a needle conduit 27 is carried from an aspiration station 28, which is transversely displaced from the conveyor 12, over one row 18 substantially at the beginning of the forward path. Means (not shown) are provided for injecting reagents into selected opentop reaction containers during their travel in the forward path, and reacted samples aspiration and readout means 30 supported over an area adjacent the ends of the upper path of the conveyor 12 are also supported to the housing 2. The analysis may be performed by spectrophotometric means included within the readout means 30 and by a flame photometer 32 mounted to the upper surface 4 of the housing 2.

Again with reference to FIGS. 1, 2 and 3, a second conveyor 36 is provided for periodic indexing in synchronism with indexing of the conveyor 12. The conveyor 36 comprises sample source delivery means for delivering sample material, e.g., human serum, to the aspiration station 28 for cooperation with the dispensing means 26. The conveyor 36 comprises container holders 38 linked together to form a conveyor having longitudinally extending, vertically disposed forward and return paths 39 and 40. The conveyor 36 is positioned such that one conveyor position is at the aspiration station 28. A vertically disposed, longitudinally extending guard wall 37 may be provided transversely displaced from the conveyor 36 remote from the conveyor 12.

Samples are delivered to the aspiration station 28 and the dispensing means positioned over a container in a container holder 38 can withdraw a requisite amount and carry aliquots of samples to a group comprising at least one reaction container along a row of the reaction conveyor 12. The need for long conduits from the sample source means 36 to the aspiration station 28 is eliminated. Preferably the forward and return paths 39 and 40 are parallel and joined at their ends by contours defined by paths of the container holders 38.

Figure 4:
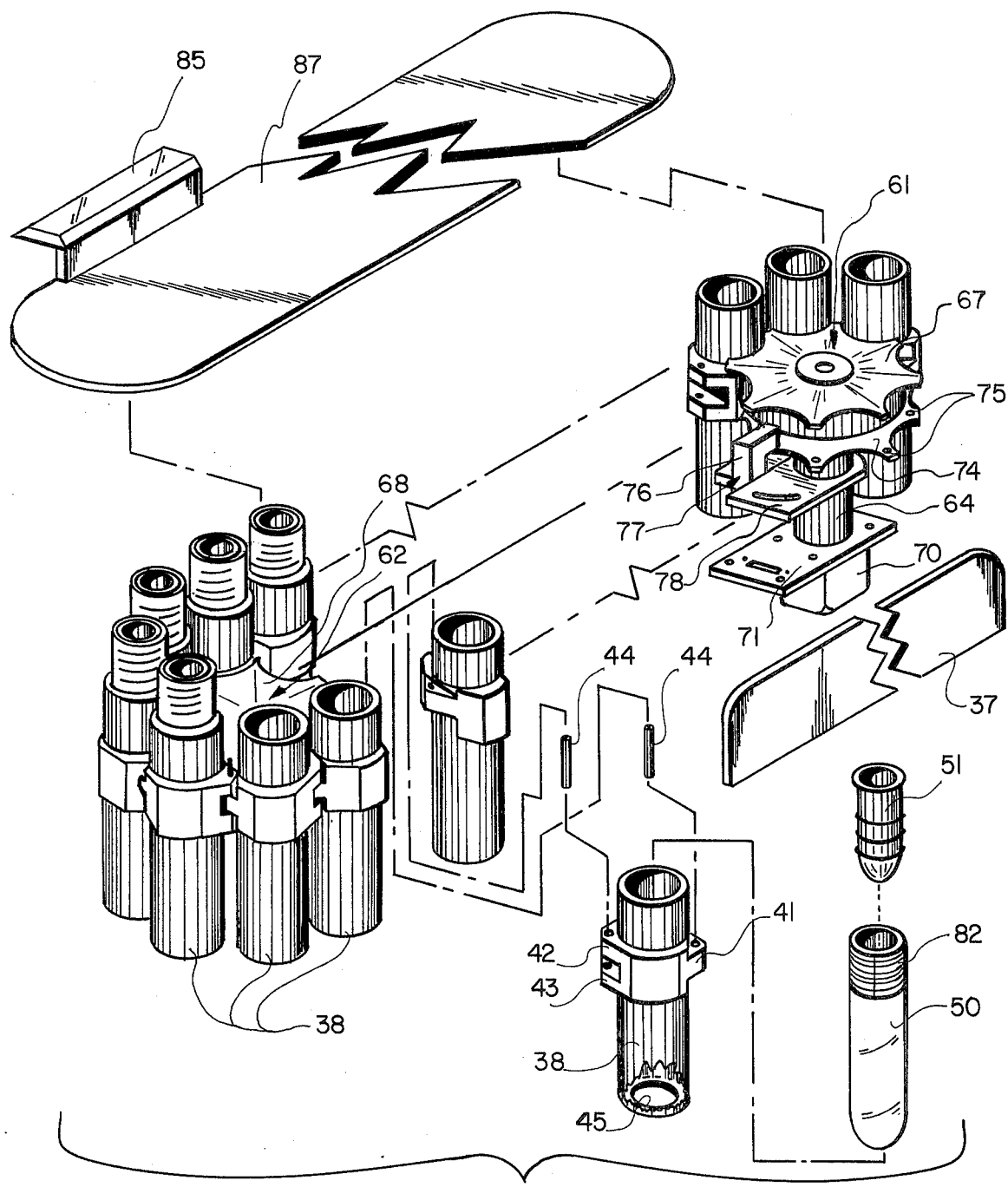
FIG. 4 is an illustration in axonometric form of details of sample conveyor means.

Referring to FIG. 4, a detail of the conveyor 36 in the preferred form is shown. Each of the sample holders 38 is provided with a first boss 41 at one point on its periphery and first and second bosses 42 and 43 vertically displaced from the first boss 42. Each of the bosses 41, 42 and 43 has a vertical bore therethrough. In this manner, adjacent containers 38 may be linked together by pins 44 so that the second conveyor 36 may be completely formed without a separate chain.

Each container holder 38 may be formed with a hole 45 in the bottom thereof to permit container-moving means 48 (FIG. 5) driven by drive means 49 to project periodically through the hole 45. Relative motion is thus provided between a container in the container holder 38 and the aspiration needle 27 (FIG. 2). After each sample is delivered to the aspiration station 28, relative motion is provided between the sample container 50 and the aspiration needle 27. The drive means 48 directs a plunger 50 through the hole 45 to move the container 50. Alternatively, other forms of relative motion such as telescoping of the needle 27 may be provided.

In the present embodiment, the container holder 38 holds a container 50 which in turn supports a sample cup 51. The container 50 is preferably from a well-known Vacutainer (trademark of Becton, Dickinson and Company) blood collection system. A Vacutainer is a well-known apparatus for drawing blood from patients. In use, the Vacutainer has a vacuum formed therein and is covered by a membrane. To draw blood from a patient, a needle is inserted in the patient's arm and another needle connected by a conduit thereto is inserted into the Vacutainer. The Vacutainer withdraws blood, and there is no danger of putting air in a patient's vein. In common practice the Vacutainer is centrifuged or otherwise handled to separate serum from whole blood. It is the serum that will comprise the sample for the present apparatus. Thus, in the present embodiment the Vacutainer may be centrifuged to provide serum, the serum decanted into the serum cup, and the sample cup 51 placed back in the container 50 for insertion in the sample container holder 38. Ease of Vacutainer and serum handling for the laboratory technician is thus maximized.

Support and drive means 61 and 62 are provided adjacent opposite longitudinal ends of the conveyor 36. Each of the means 61 and 62 is in a bearing and each supports a sprocket means 67 and 68, respectively. The sprockets 67 and 68 support the chain of container holders 38. The drive means 62 is driven by a motor 70 connected thereto and preferably mounted by a plate 71 to the underside of the upper surface 4 (FIG. 1).

The sprocket means 67 may include a set of radially disposed teeth 74, each having an aperture 75 therein. A photosensor means 76 is provided including light source and receptor means, each disposed on an opposite side of the plane of rotation of the teeth 74. The cooperation of the apertures 75 and the light path of the photosensor means 76 defines optical limit switch means 77. The optical limit switching is utilized for assisting in stopping the motor 70 after it is commanded to rotate such that the conveyor 36 is indexed one position. An adjustment plate 78 is connected to the drive means 71 for setting a reference angular position of the sprocket means 67 at which an aperture 75 of a tooth 74 is in registration with the light path defined by the photosensor means 76.

A bar code label 82 is affixed to the sample container 50. As seen further with respect to FIGS. 1, 2, 3 and 4, bar code reader means 80 are provided. Bar codes are well known and bar codes labels such as those provided under the Trademark Codabar of the Monarch Marking System, Division of Pitney Bowes Incorporated could be utilized. The read head 80 provides for relative motion of optical source and reception means and the bar code label 82 affixed to one of the containers 50. The bar code reading is stored and used to identify which sample is progressing to the aspiration station 28 and eventually to the readout means 30. The reading means 80 is longitudinally displaced from the aspiration station 28. Guard means 85 are positioned to prevent removal of a sample from the conveyor 36 between reading and aspiration. The guard means 85 if mounted on a plate 87, which may comprise a cover mounted over the interior of the loop formed by the conveyor 36 and the support and drive means 61 and 62.

Figure 5:
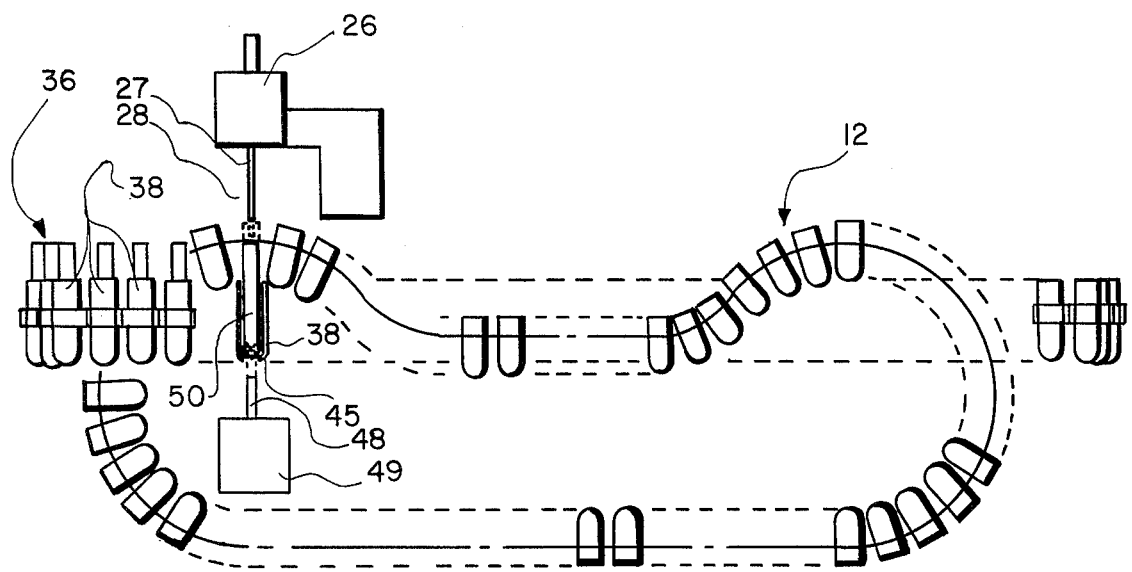
FIG. 5 is a mechanical schematic diagram illustrating the spatial relationships of the loop conveyor and the reaction conveyor.

Referring further to FIG. 5 which is a mechanical schematic diagram, the support of the conveyor 36 with respect to the aspiration means 26 and the conveyor 12 is illustrated. The conveyor 36 is mounted on the upper surface 4 such that the samples are maintained at a vertical level in registration with the level of the row into which the dispensing means 26 dispenses samples.

Figure 6:
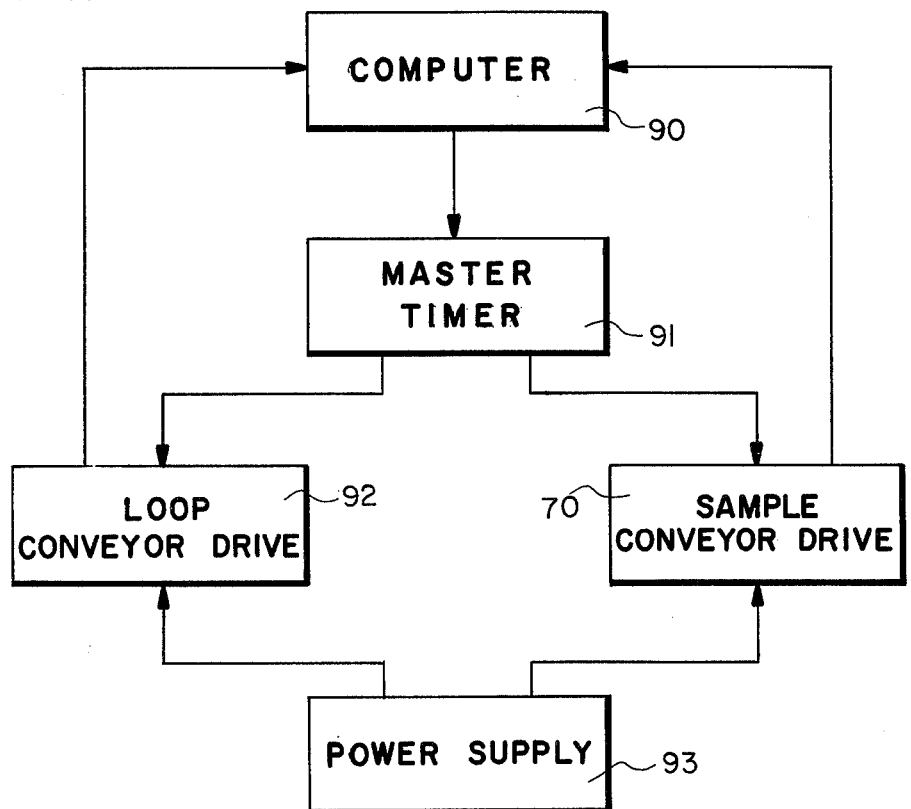
FIG. 6 is a block diagramatic representation of operating and control circuitry for the present apparatus.

FIG. 6 is a block diagrammatic representation of a control scheme for the present system. A computer 90 may comprise control means of the above-cited patents to Moran or other well-known control means. The computer 90 is coupled to a master timer 91 which provides command signals in predeterminedly phased time relationships to the sample conveyor drive means, namely the motor 70 and to a reaction loop conveyor drive 92 to enable rotation. A power supply 93 is connected to the drives 70 and 92 are connected to the computer 90 to provide positional information. The feedback signals may be provided from such means as the optical limit switching means 77 (FIG. 4) or from conventional means.

What is thus provided is an automatic chemical testing apparatus incorporating improved sample handling means and providing an improved interaction between a sample source and reaction conveyor means.

What is claimed as new and desired to be secured by Letters Patent of the United States is:

1. In a chemical testing apparatus including reaction means having a plurality of sections defining rows and each containing a plurality of reaction containers therein, said rows extending in a transverse direction and being mounted for movement in a longitudinal direction in a forward path from a beginning thereof at which aliquots of samples are dispensed into reaction containers in a first section through the forward path to readout means at which reacted contents of reaction containers are analyzed, an aspiration station transversely displaced from said reaction means and in longitudinal registration with said first section, sample source means including a plurality of sample holders, each sample holder for moving a sample, sample indexing means for indexing said sample holders to successive positions in said sample source means, means mounting said sample source means such that one position thereof is at said aspiration station, drive means for driving said sample indexing means, and control means coupled to said drive means for indexing said sample holders in synchronism with indexing of said sections in said reaction means.

2. The improvement of claim 1 wherein said sample source means comprises a conveyor and wherein said sample holders are linked together to form a conveyor.

3. The improvement according to claim 2 wherein said sample holders comprise holders for receiving tubes for containing samples.

4. The improvement according to claim 3 wherein said conveyor is mounted adjacent to said reaction means and transversely displaced to one side thereof and comprises longitudinally extending forward and return paths.

5. The improvement according to claim 4 wherein said sample holders are dimensioned and said conveyor is mounted such that samples are presented at said aspiration station in vertical registration with the group of reaction containers, whereby delivery of aliquots to the group of reaction containers is facilitated.

6. In a chemical testing apparatus including an endless loop reaction conveyor mounted in a predetermined spatial relationship to a housing, said reaction conveyor comprising a plurality of sections, each section extending in a transverse direction for movement in a longitudinal direction, and reaction containers supported in each of said sections, and means for aspirating a sample at an aspiration station and delivering to one section aliquots of the sample, the improvement comprising means defining the aspiration station transversely displaced from said reaction conveyor and in longitudinal registration with said one section, a sample conveyor mounted to said housing and comprising a plurality of means for holding samples, means for indexing said sample conveyor, said sample conveyor being mounted such that one position to which said means for holding samples are individually indexed is at said aspiration station, and control means for synchronizing indexing of said reaction conveyor and said sample conveyor.

7. The improvement of claim 6 wherein said sample conveyor is formed with parallel, longitudinally extending forward and return paths and is transversely displaced from said reaction conveyor.

8. The improvement according to claim 6 wherein said means for holding samples comprise vertically extending means for receiving tubes for containing samples.

9. The improvement of claim 8 wherein each of said means for holding samples has bosses extending from its periphery, said bosses being oppositely disposed and vertically displaced from each other, and wherein each of said means for holding samples are substantially identically formed, whereby said means for holding samples fit together to form an endless loop, and means linking adjacent means for holding sample at said bosses, whereby said sample conveyor is formed without a chain.

10. The improvement according to claim 6 wherein said means for indexing comprises sprocket means positioned in said sample conveyor at a contour linking said forward and return paths, said sprocket means having teeth formed for mating with said means for holding samples, and a motor mechanically coupled to said sprocket means and electrically coupled to said control means.

11. The improvement according to claim 10 wherein said sprocket means further comprises a set of teeth, each having an aperture therein, and photosensor means having a light path positioned to be broken by rotation of a tooth and reestablished through one of said apertures for indicating indexing of the sample conveyor.

12. The improvement according to claim 11 including means for adjusting the relative position of said photosensor means and said sprocket means, whereby a reference angular position of said sprocket means may be established.

13. The improvement according to claim 8 wherein each of said means for holding samples is formed with a hole in registration with an opening in which said tubes are inserted, and wherein means are provided at said aspiration station for periodically directing driving means through said hole, whereby relative motion is provided between each of said tubes and means for aspiration of samples.

14. The improvement of claim 7 wherein bar code labels are provided carried by each of said means for holding samples and wherein bar code reading means are mounted to said housing longitudinally displaced from said aspiration station ahead thereof with respect to the forward path of said sample conveyor.

15. The improvement of claim 14 further comprising guard means mounted for preventing removal of samples from said sample conveyor between said bar code reading means and said aspiration station.

16. The improvement according to claim 6 wherein said sample conveyor is mounted to maintain a sample at said aspiration station in vertical registration with the said one row of said reaction conveyor.

17. The improvement according to claim 6 wherein said means for holding samples comprises a vertically extending sample holder, a blood collection tube received in said sample holder and a sample cup received in said blood collection tube.

18. The improvement according to claim 10 including further sprocket means at an opposite contour of said sample conveyor positioned such that said sample conveyor is supported by both of said sprocket means.

* * * * *